United States Patent
Blumenfeld

(10) Patent No.: US 8,992,941 B2
(45) Date of Patent: Mar. 31, 2015

(54) METHOD FOR TREATMENT OF ESOPHAGEAL SPASM

(75) Inventor: Andrew M. Blumenfeld, Del Mar, CA (US)

(73) Assignee: Allergan, Inc., Irvine, CA (US)

( * ) Notice: Subject to any disclaimer, the term of this patent is extended or adjusted under 35 U.S.C. 154(b) by 314 days.

(21) Appl. No.: 13/542,479

(22) Filed: Jul. 5, 2012

(65) Prior Publication Data

US 2013/0011504 A1    Jan. 10, 2013

Related U.S. Application Data

(60) Provisional application No. 61/505,981, filed on Jul. 8, 2011.

(51) Int. Cl.
| | | |
|---|---|---|
| A61K 35/74 | (2006.01) | |
| A61K 39/08 | (2006.01) | |
| A61K 38/48 | (2006.01) | |

(52) U.S. Cl.
CPC ................... *A61K 38/4893* (2013.01)
USPC ...................... 424/239.1; 424/780

(58) Field of Classification Search
CPC ... A61K 9/0019; A61K 9/0024; A61K 35/74; A61K 38/4893
USPC .............................. 424/239.1, 780
See application file for complete search history.

(56) References Cited

U.S. PATENT DOCUMENTS

| | | | |
|---|---|---|---|
| 5,437,291 A | 8/1995 | Pasricha et al. |
| 5,670,484 A | 9/1997 | Binder |
| 5,714,468 A | 2/1998 | Binder |
| 5,766,605 A | 6/1998 | Sanders et al. |
| 5,989,545 A | 11/1999 | Foster et al. |
| 6,063,768 A | 5/2000 | First |
| 6,113,915 A | 9/2000 | Aoki et al. |
| 6,139,845 A | 10/2000 | Donovan |
| 6,143,306 A | 11/2000 | Donovan |
| 6,265,379 B1 | 7/2001 | Donovan |
| 6,299,893 B1 | 10/2001 | Schwartz et al. |
| 6,306,403 B1 | 10/2001 | Donovan |
| 6,306,423 B1 | 10/2001 | Donovan et al. |
| 6,312,708 B1 | 11/2001 | Donovan |
| 6,328,977 B1 | 12/2001 | Donovan |
| 6,358,513 B1 | 3/2002 | Voet et al. |
| 6,365,164 B1 | 4/2002 | Schmidt |
| 6,395,277 B1 | 5/2002 | Graham |
| 6,423,319 B1 | 7/2002 | Brooks et al. |
| 6,458,365 B1 | 10/2002 | Aoki et al. |
| 6,464,986 B1 | 10/2002 | Aoki et al. |
| 7,658,933 B2 | 2/2010 | Foster et al. |
| 7,659,092 B2 | 2/2010 | Foster et al. |

FOREIGN PATENT DOCUMENTS

WO    WO 2007/138339    12/2007

OTHER PUBLICATIONS

Table of Contents for Diseases of the Esophagus (2010), vol. 23, No. 7.*
Bartolomei, Luigi et al, Botulinum Toxin Type A: An Effective Treatment to Restore Phonation in Laryngectomized Patients Unable to Voice, Neurol Sci, 2011, 443-447, 32.
Bashashati, M et al, Botulinum Toxin in the Treatment of Diffuse Esophageal Spasm, Diseases of the Esophagus, 2010, 554-560, 23.
Chao, Siew-Shuen et al, Management of Pharyngoesophageal Spaem with Botox, Otolaryngologic Clinics of North America, 2004, 559-566, 37.
Martin, Storr et al, Long-Term Treatment of Symptomatic Diffuse Esophageal Spasm by Injection of Botulinum Toxin (BTX), Digestive Disease, 2003, S1639, 2003.
Miller, Larry et al, Treatment of Symptomatic Nonachalasia Esophageal Motor Disorders with Botulinum Toxin Injection at the Lower Esophagael Sphincter, Digestive Diseases and Sciences, 1996, 2025-2031, 41(10).
Nebendahl, JC et al, Effective Treatment of Diffuse Esophageal Spasm (DES) byEndoscopic Injection of Botulinum Toxin (BTX), Gastroenterology, Apr. 1998, G0984, 114(4).
Rees, Catherine, In-Office Transnasal Esophagoscope-Guided Botulinum Toxin, Current Opinion in Otolaryngology & Head and Neck Surgery, Dec 2007, 409-411, 15(6).
Storr, Martin et al, Treatment of Symptomatic Diffuse Esophageal Spasm by Endoscopic Injections of Botulinum Toxin: A Prospective Study With Long-Term Follow-up, Gastrointestinal Endoscopy, 2001, 754-759, 54(6).

* cited by examiner

*Primary Examiner* — Susan Hoffman
(74) *Attorney, Agent, or Firm* — Brigitte C. Phan; Ted A. Chan; Debra D. Condino

(57) ABSTRACT

The present invention relates to methods of treating esophageal spasms using *botulinum* toxins.

10 Claims, No Drawings

METHOD FOR TREATMENT OF ESOPHAGEAL SPASM

CROSS REFERENCE TO RELATED APPLICATION

This patent application claims priority pursuant to 35 U.S.C. §119(e) to U.S. Provisional Patent Application Ser. No. 61/505,981 filed Jul. 8, 2011, which is hereby incorporated by reference in its entirety.

FIELD OF THE INVENTION

The present invention relates to methods and compositions for treating esophageal spasm using *botulinum* toxins.

BACKGROUND

Viral conjunctivitis, known commonly as pink eye, is a common highly contagious disease Peristalsis is the distinctive pattern of smooth muscle contractions that propel foodstuffs distally through the esophagus and intestines. First described by Bayliss and Starling (J. Physio (Lond) 24:99-143, 1899) as a form of motility in which there is contraction above and relaxation below a segment being stimulated, it is unaffected by vagotomy or sympathectomy, indicating its mediation by the intestine's local, intrinsic nervous system. Peristalsis is a manifestation of two major reflexes within the enteric nervous system that are stimulated by a bolus of foodstuff in the lumen; mechanical distension and perhaps mucosal irritation stimulate afferent enteric neurons. These sensory neurons synapse with two sets of cholinergic interneurons, which leads to two distinct effects: one group of interneurons activates excitatory motor neurons above the bolus. These neurons, which can release acetylcholine and substance P, stimulate contraction of smooth muscle above the food bolus. Another group of interneurons activates inhibitory motor neurons that stimulate relaxation of smooth muscle below the bolus. These inhibitor neurons appear to use nitric oxide, vasoactive intestinal peptide and ATP as neurotransmitters.

Esophageal spasms are an uncoordinated series of muscle contractions that prevent food from traveling properly from the esophagus to the stomach. These spasms can be very painful, with chest pain a common symptom. Broadly, esophageal spasm can be subdivided into 2 distinct entities: diffuse esophageal spasm (DES), in which contractions are uncoordinated, and nutcracker esophagus, in which contractions proceed in a coordinated manner, but the amplitude is excessive. Symptoms can include dysphagia, regurgitation, and noncardiac chest pain. Because of the vague symptoms and difficulty in diagnosis, esophageal spasm is often undiagnosed and under-treated. Many patients with manometric and radiologic aberrations may not display any appreciable symptoms. Currently, manometry is the best diagnostic modality. Treatment includes calcium channel blockers, *botulinum* toxin, nitrates, tricyclic antidepressants, dilatation, myotomy, and esophagectomy.

Pathophysiology

The esophagus is comprised of 2 layers of muscle, the inner circular and the outer longitudinal layers. Arbitrarily, the esophagus can be divided into 3 zones, each with separate yet integrated anatomy and physiology.

Esophageal Zones

Upper zone: Comprised entirely of striated muscle, this zone initiates the contractions that propel the food bolus down the esophagus. The upper esophageal sphincter (UES; the cricopharyngeus muscle), is located in the upper zone. When functioning properly, the esophagus can detect the presence of a food bolus at the UES and then coordinate progression of the food down the esophagus to the stomach. When this does not occur in a coordinated fashion, the patient can develop symptoms of esophageal spasm. The UES is contracted tonically. Manometric evaluation of the UES reveals constant spiking activity. As food is sensed at the UES, the laryngeal muscles contract to move the cricoid cartilage anteriorly. The tonic contraction of the UES is inhibited, opening the UES to allow passage of food. The inner circular muscles and longitudinal muscles of the remainder of the upper zone then propel the food. To accomplish this, the longitudinal muscles must contract, followed immediately by contraction of the circular muscles. At the end of the upper zone, the initial wave dies out as another wave starts, propelling the food down to the middle zone. The nucleus solitarius in the brainstem controls swallowing in the upper zone.

Middle zone: Comprised of striated and smooth muscles, the inner circular muscle layer and the outer longitudinal muscle layer work in conjunction to propel the food bolus. The middle zone propels the food bolus from the upper zone to the lower zone. This segment consists of 2 muscle layers, an inner circular and outer longitudinal layer. Within the middle zone the striated muscle transitions to smooth, or involuntary, muscle. The wave propagates down the esophagus by coordinated contractions. Again, the longitudinal muscles must contract before the circular muscle contracts. Furthermore, contraction of the muscles must proceed caudally in an organized manner. If the muscle contraction is not orderly, the food bolus cannot progress. Gravity pulls the food caudally in concert with the organized contractions of the muscles.

Lower zone: The lower segment is known as the lower esophageal sphincter (LES), a thickening of the smooth muscle that is contracted tonically to prevent reflux. At rest, the pressure in the LES is usually 15-25 mm Hg. For food to pass into the stomach, the LES relaxes. Tonically, this muscle is contracted and must relax to allow food to pass. Failure of the LES to relax to allow a food bolus to pass is termed achalasia.

Diffuse Esophageal Spasm (DES)

Simplistically, DES occurs when the propagative waves do not progress correctly. Usually, several segments of the esophagus contract simultaneously, preventing the propagation of the food bolus. The usual presentation is intermittent dysphagia with occasional chest pain. Myotomy, which is performed only in extreme cases, can relieve the uncoordinated contractions.

Nutcracker Esophagus

Nutcracker esophagus occurs when the amplitude of the contractions exceeds 2 standard deviations from normal. The contractions proceed in an organized manner, propelling food down the esophagus. These patients often present with chest pain, but they present with dysphagia less often than patients with DES. Because the progression of the contractions occurs normally, patients often do not benefit from a myotomy. Even though the increased amplitude of the contractions can be demonstrated using manometry, the symptoms often do not correlate with the manometrically documented contractions. The symptoms of DES and nutcracker esophagus may overlap and can be distinguished only by motility study.

Imaging Studies

Barium swallow has proven useful in the diagnosis of esophageal spasm—DES has a characteristic appearance of multiple simultaneous contractions. This is often referred-to as a corkscrew appearance. Unlike in DES, barium swallow results for nutcracker esophagus are not specific.

Nino-Murcia and colleagues demonstrated thickening of the esophagus with CT scan studies in patients with esophageal spasm. Muscular hypertrophy has been documented in some patients with DES and nutcracker esophagus. The hypertrophy of the muscle wall is the cause of the increased thickness that is observed on CT scan images. The normal thickness of the esophagus is less than 3 mm. Many other disease processes, including malignancy, cause thickening of the esophagus that can be seen radiographically. Thus, thickening of the esophagus seen on CT scan images should prompt further workup. Even in patients with symptoms consistent with esophageal spasm, thickening seen on CT scan images should not be dismissed as muscular hypertrophy secondary to the esophageal spasms without further investigation.

Catheter-based high-frequency intraluminal ultrasound imaging assesses both the sensory function and the motor function of the esophagus. This imaging modality may be useful to distinguish between DES, nutcracker esophagus, and achalasia.

Manometry is the best modality to help diagnose DES. The classic definition is more than 2 uncoordinated contractions during 10 consecutive wet swallows (20% simultaneous esophageal contractions during standardized stationary motility testing). At least one peristaltic contraction must be present. Artificial neural networks may be useful in the recognition and objective classification of primary esophageal motor disorders investigated with stationary esophageal manometry recordings.

Increased release of acetylcholine appears to be a factor in DES, but the triggering event is not known. Other theories include gastric reflux or a primary nerve or motor disorder. Microvascular compression of the Vagus nerve in the brainstem has been demonstrated in current research as the possible triggering event. Medical therapy may focus on these blood vessels instead of on the muscles in the esophagus.

Medical and surgical options are available for the treatment of DES and nutcracker esophagus and have been used with moderate success. Medical treatment typically consists of calcium channel blockers, tricyclic antidepressants, nitrates, *botulinum* toxin, and dilatation. These conditions are usually not progressive but may interfere with the patient's quality of life. Calcium channel blockers can reduce the amplitude of the contractions. In patients with nutcracker esophagus, calcium channel blockers effectively reduce the amplitude of the contractions, but may not lessen chest pain. Traditionally, calcium channel blockers were thought to decrease the contractions. Nitrates also have been used with some success. The mechanism of action is unknown but may be related to decreasing vasospasm in the brainstem, similar to calcium channel blockers. Some patients benefit from sublingual nitroglycerin for acute symptoms of esophageal spasm.

Tricyclic antidepressants, specifically imipramine, have been shown to decrease chest pain with no apparent cause on angiogram. Studies specifically evaluating nutcracker esophagus are not yet available.

For extreme cases, operative treatment usually involves a myotomy. Myotomy relieves symptoms by eliminating the effectiveness of the contractions. The myotomy should extend the entire length of the involved segment, which should be determined preoperatively with manometry. Furthermore, the myotomy should extend through the LES to help prevent dysphagia postoperatively by preventing outlet obstruction. Finally, an antireflux procedure should be performed concomitantly.

Myotomy should be used with caution in patients with nutcracker esophagus because it may worsen the symptoms. Myotomy reduces the amplitude of the contractions, but this does not consistently improve symptoms, especially if the primary complaint is pain. Furthermore, dysphagia can develop or worsen after myotomy because the effectiveness of the propagative waves is eliminated, leaving gravity to propel food caudally. As a last resort, esophagectomy can be used to relieve symptoms. The esophagus is resected, and the stomach, small intestine, or colon is used to restore the continuity of the GI tract. Morbidity and mortality of esophagectomy are substantial; therefore, this should be performed only after other treatments have been exhausted.

*Botulinum* toxin type A is the most lethal natural biological agent known to man. About 50 picograms of *botulinum* toxin type A (available from Allergan, Inc., of Irvine, Calif. under the tradename BOTOX®) is an $LD_{50}$ in mice. One unit (U) of *botulinum* toxin is defined as the $LD_{50}$ upon intraperitoneal injection into female Swiss Webster mice weighing 18-20 grams each. Seven immunologically distinct *botulinum* neurotoxins have been characterized, these being respectively *botulinum* neurotoxin serotypes A, B, $C_1$, D, E, F and G, each of which is distinguished by neutralization with type-specific antibodies. The different serotypes of *botulinum* toxin vary in the animal species that they affect and in the severity and duration of the paralysis they evoke. The *botulinum* toxins apparently bind with high affinity to cholinergic motor neurons, are translocated into the neuron and block the release of acetylcholine.

*Botulinum* toxins have been used in clinical settings for the treatment of neuromuscular disorders characterized by hyperactive skeletal muscles. *Botulinum* toxin type A has been approved by the U.S. Food and Drug Administration for the treatment of blepharospasm, strabismus, hemifacial spasm, cervical dystonia, and migraine headaches. *Botulinum* toxin type B has also been approved by the FDA for the treatment of cervical dystonia. Clinical effects of peripheral intramuscular *Botulinum* toxin type A are usually seen within one week of injection. The typical duration of symptomatic relief from a single intramuscular injection of *Botulinum* toxin type A averages about three months.

It has been reported that *Botulinum* toxin type A has been used in clinical settings as follows:

about 75-125 U (U) of BOTOX® per intramuscular injection (multiple muscles) to treat cervical dystonia;

5-10 U of BOTOX® per intramuscular injection to treat glabellar lines (brow furrows) (5 U injected intramuscularly into the procerus muscle and 10 U injected intramuscularly into each corrugator supercilii muscle);

about 30-80 U of BOTOX® to treat constipation by intrasphincter injection of the puborectalis muscle;

about 1-5 U per muscle of intramuscularly injected BOTOX® to treat blepharospasm by injecting the lateral pre-tarsal orbicularis oculi muscle of the upper lid and the lateral pre-tarsal orbicularis oculi of the lower lid.

to treat strabismus, extraocular muscles have been injected intramuscularly with between about 1-5 U of BOTOX®, the amount injected varying based upon both the size of the muscle to be injected and the extent of muscle paralysis desired (i.e. the amount of diopter correction desired).

to treat upper limb spasticity following stroke by intramuscular injections of BOTOX® into five different upper limb flexor muscles, as follows:
 (a) flexor digitorum profundus: 7.5 U to 30 U
 (b) flexor digitorum sublimis: 7.5 U to 30 U
 (c) flexor carpi ulnaris: 10 U to 40 U
 (d) flexor carpi radialis: 15 U to 60 U
 (e) biceps brachii: 50 U to 200 U.

Each of the five indicated muscles has been injected at the same treatment session, so that the patient receives from 90 U to 360 U of upper limb flexor muscle BOTOX® by intramuscular injection at each treatment session.

To treat migraine, pericranial (symmetrically into glabellar, frontalis and temporalis muscles) injection of 25 U of BOTOX® has showed significant benefit as a prophylactic treatment compared to vehicle as measured by decreased measures of migraine frequency, maximal severity, associated vomiting and acute medication use over the three month period following the 25 U injection.

Additionally, intramuscular *Botulinum* toxin has been used in the treatment of tremor in patients with Parkinson's disease, although it has been reported that results have not been impressive. Marjama-Jyons, J., et al., Tremor-Predominant Parkinson's Disease, Drugs & Aging 16(4); 273-278:2000.

In addition to having pharmacologic actions at the peripheral location, *botulinum* toxins may also have inhibitory effects in the central nervous system. Work by Weigand et al., Naunyn-Schmiedeberg's Arch. Pharmacol. 1976; 292, 161-165, and Habermann, Naunyn-Schmiedeberg's Arch. Pharmacol. 1974; 281, 47-56 showed that *Botulinum* toxin is able to ascend to the spinal area by retrograde transport. As such, a *Botulinum* toxin injected at a peripheral location, for example intramuscularly, may be retrograde transported to the spinal cord.

U.S. Pat. No. 5,989,545 discloses that a modified Clostridial neurotoxin or fragment thereof, preferably a *Botulinum* toxin, chemically conjugated or recombinantly fused to a particular targeting moiety can be used to treat pain by administration of the agent to the spinal cord.

A *Botulinum* toxin has also been proposed for the treatment of rhinorrhea, hyperhidrosis and other disorders mediated by the autonomic nervous system (U.S. Pat. No. 5,766,605), tension headache, (U.S. Pat. No. 6,458,365), migraine headache (U.S. Pat. No. 5,714,468), post-operative pain and visceral pain (U.S. Pat. No. 6,464,986), pain treatment by intraspinal toxin administration (U.S. Pat. No. 6,113,915), Parkinson's disease and other diseases with a motor disorder component, by intracranial toxin administration (U.S. Pat. No. 6,306,403), hair growth and hair retention (U.S. Pat. No. 6,299,893), psoriasis and dermatitis (U.S. Pat. No. 5,670,484), injured muscles (U.S. Pat. no. 6,423,319, various cancers (U.S. Pat. No. 6,139,845), pancreatic disorders (U.S. Pat. No. 6,143,306), smooth muscle disorders (U.S. Pat. No. 5,437,291, including injection of a *botulinum* toxin into the upper and lower esophageal, pyloric and anal sphincters)), prostate disorders (U.S. Pat. No. 6,365,164), inflammation, arthritis and gout (U.S. Pat. No. 6,063,768), juvenile cerebral palsy (U.S. Pat. No. 6,395,277), inner ear disorders (U.S. Pat. No. 6,265,379), thyroid disorders (U.S. Pat. No. 6,358,513), parathyroid disorders (U.S. Pat. No. 6,328,977). Additionally, controlled release toxin implants are known (see e.g. U.S. Pat. Nos. 6,306,423 and 6,312,708).

DESCRIPTION OF EXEMPLARY EMBODIMENTS

Embodiments of the invention utilize a method of administering compositions comprising *Botulinum* toxins and like substances to treat, for example, abnormal gastro-intestinal motility such as, for example, esophageal spasms, and the like. In order to create a clear passage for a food bolus, the esophagus can be treated as one large muscle and, in an embodiment, the toxin is administered with the largest doses distally and progressively lower doses as the administration sites move proximally. In certain embodiments, the method of administration can be, for example, endoscopic injection, implant, or the like.

The following definitions apply herein:

"About" means approximately or nearly and in the context of a numerical value or range set forth herein means .+-.10% of the numerical value or range recited or claimed.

"Above" in the context of the invention means a point along the esophagus closer to the mouth as compared to a reference point further from the mouth.

"Affliction" includes a disease, disorder, problem and/or a cosmetically undesirable state or condition in an individual.

"Alleviating" means a reduction in the occurrence of a symptom related to esophageal spasms. Thus, alleviating includes some reduction, significant reduction, near total reduction, and total reduction of a symptom related to esophageal spasms. An alleviating effect may not appear clinically for between 1 to 7 days after administration of a *Botulinum* toxin to a patient.

"*Botulinum* toxin" means a *Botulinum* neurotoxin as either pure toxin (i.e. about 150 kDa weight molecule) or as a complex (i.e. about 300 to about 900 kDa weight complex comprising a neurotoxin molecule and one or more associated non-toxic molecules), and excludes *botulinum* toxins which are not neurotoxins such as the cytotoxic *botulinum* toxins C2 and C3, but includes recombinantly made, hybrid, modified, and chimeric *botulinum* toxins.

"Endopeptidase" as used herein means a biologically active molecule with a specific affinity for a cell surface receptor of sensory neurons (also known as afferent or receptor neurons). Sensory neurons carry nerve impulses from receptors or sense organs towards the central nervous system. Endopeptidases such as TVEMPs decrease the effects of sensory afferents, including conditions that are predominantly motor in origin. See, for example, U.S. Pat. No. 7,658,933 to Foster et al., titled "Non-Cytotoxic Protein Conjugates"; U.S. Pat. No. 7,659,092 to Foster et al., titled "Fusion Proteins"; and U.S. Ser. No. 12/303,078 to Foster et al., titled "Treatment of Pain," all incorporated entirely by reference. In addition, endopeptidases can modulate pain associated with multiple medical conditions.

"Improved patient function" means an improvement measured by factors such as reduced pain, reduced time spent in bed, increased ambulation, healthier attitude, more varied lifestyle and/or healing permitted by normal muscle tone. Improved patient function is synonymous with an improved quality of life (QOL). QOL can be assessed using, for example, the known SF-12 or SF-36 health survey scoring procedures. SF-36 assesses a patient's physical and mental health in the eight domains of physical functioning, role limitations due to physical problems, social functioning, bodily pain, general mental health, role limitations due to emotional problems, vitality, and general health perceptions. Scores obtained can be compared to published values available for various general and patient populations.

"Local administration" or "locally administering" means administration (i.e. by a subcutaneous, intramuscular, subdermal or transdermal route) of a pharmaceutical agent to or to the vicinity of a dermal or subdermal location of a patient.

"Treating" means to alleviate (or to eliminate) at least one symptom related to esophageal spasms, either temporarily or permanently.

Traditionally, only small doses of *Botulinum* toxin have been injected at the level of the LES. Embodiments of the invention employ a dose of *Botulinum* toxin, such as, for example, type A, of 100 U diluted in 4 mL of preservative free normal saline.

In embodiments of the invention, *botulinum* administrations into the muscle wall are performed as follows:

A first administration of between 10 and 50 U at the level of the LES;

A second administration of between 10 and 30 U above the LES;

A third administration of between 15 and 25 U above the second administration;

Certain embodiments comprise a fourth administration of between 10 and 20 U above the third administration;

Certain embodiments comprise a fifth administration of between 5 and 15 U above the fourth administration; and Certain embodiments comprise a sixth administration of between 2 and 10 U above the fifth administration.

In an embodiment of the invention, endoscopic injections into the muscle wall are performed as follows:

30 U at the level of the LES;
22.5 U 6 cm above the LES;
17.5 U 12 cm above the LES;
15 U 18 cm above the LES;
10 U 24 cm above the LES;
5 U 30 cm above the LES;
Total dose 100 U.

In certain embodiments, the distance between toxin administration sites can be modified. For example, the distances between administration sites can be increased, or decreased, or the like. Depending on the length of the esophagus additional administrations can be performed at, for example, 6 cm intervals, or larger intervals, or smaller intervals, or the like. The space interval allows for diffusion of the toxin in local bands producing a gradient of weakness that mimics peristalsis. The *Botulinum* toxin can be administered in an amount of between about 1 unit and about 3,000 U and the effect of the administration can persist for between about 1 month and about 5 years. The dose can be adjusted with serial injections to ensure that only partial weakness is produced. If dysphagia occurs the dose can be reduced.

Administrations can be performed, for example, to the esophagus muscle wall, to the LES, at the level of the LES, just above the LES, and the like.

The *botulinum* toxin can be selected from the group consisting of *botulinum* toxin types A, B, C, D, E, F and G. *Botulinum* toxin type A is a preferred *botulinum* toxin.

*Botulinum* toxins for use according to the present invention can be stored, for example, in lyophilized or vacuum dried form in containers under vacuum pressure, or as stable liquids. Prior to lyophilization the *Botulinum* toxin can be combined with pharmaceutically acceptable excipients, stabilizers and/or carriers, such as albumin. The lyophilized material can be reconstituted, for example, with saline or water or the like, to create a solution or composition containing the *botulinum* toxin to be administered to the patient.

Exemplary, commercially available, *Botulinum* toxin containing compositions include, but are not limited to, BOTOX® (*Botulinum* toxin type A neurotoxin complex with human serum albumin and sodium chloride) available from Allergan, Inc., of Irvine, Calif. in 100 unit vials as a lyophilized powder to be reconstituted with 0.9% sodium chloride before use), DYSPORT® (*Clostridium Botulinum* type A toxin haemagglutinin complex with human serum albumin and lactose in the formulation, available from Ipsen Limited, Berkshire, U.K. as a powder to be reconstituted with 0.9% sodium chloride before use) which can be used at about 3 to about 4 times the amounts of BOTOX® as set forth herein in each instance, and MYOBLOC® (an injectable solution comprising *Botulinum* toxin type B, human serum albumin, sodium succinate, and sodium chloride at about pH 5.6, available from Solstice Neurosciences, Inc., South San Francisco, Calif.) which can be used at about 30 to about 50 times the amounts of BOTOX® as set forth herein in each instance, as known in the art. XEOMIN® (a 150 kDa *Botulinum* toxin type A formulation available from Merz Pharmaceuticals, Potsdam, Germany) is another useful neurotoxin which can be used at about 1 to about 2 times the amounts of BOTOX® as set forth herein in each instance.

In additional embodiments, no less than about 10 U and no more about 400 U of BOTOX®; no less than about 30 U and no more than about 1600 U of DYSPORT®, and; no less than about 250 U and no more than about 20000 U of MYOBLOC® are administered per site, per patient treatment session.

In still further embodiments, no less than about 20 U and no more about 300 U of BOTOX®; no less than about 60 U and no more than about 1200 U of DYSPORT®, and; no less than about 1000 U and no more than about 15000 U of MYOBLOC® are administered per site, per patient treatment session.

Although the composition may only contain a single type of *Botulinum* toxin, such as, for example, type A, as the active ingredient to suppress neurotransmission, other therapeutic compositions may include two or more types of *Botulinum* toxins. For example, a composition administered to a patient may include *Botulinum* toxin type A and *Botulinum* toxin type B. Administering a single composition containing two different neurotoxins can permit the effective concentration of each of the neurotoxins to be lower than if a single neurotoxin is administered to the patient while still achieving the desired therapeutic effects. The composition administered to the patient may also contain other pharmaceutically active ingredients, such as, for example, protein receptor or ion channel modulators, or the like, in combination with the neurotoxin or neurotoxins. These modulators can contribute to the reduction in neurotransmission between the various neurons. For example, a composition may contain gamma aminobutyric acid (GABA) type A receptor modulators that enhance the inhibitory effects mediated by the GABAA receptor. The GABAA receptor inhibits neuronal activity by effectively shunting current flow across the cell membrane. GABAA receptor modulators may enhance the inhibitory effects of the GABAA receptor and reduce electrical or chemical signal transmission from the neurons. Examples of GABAA receptor modulators include benzodiazepines, such as diazepam, oxazepam, lorazepam, prazepam, alprazolam, halazepam, chlordiazepoxide, and clorazepate. Compositions may also contain glutamate receptor modulators that decrease the excitatory effects mediated by glutamate receptors. Examples of glutamate receptor modulators include agents that inhibit current flux through AMPA, NMDA, and/or kainate types of glutamate receptors. The compositions may also include agents that modulate dopamine receptors, such as antipsychotics, norepinephrine receptors, and/or serotonin receptors. Compositions of embodiments of the invention can also include agents that affect ion flux through voltage gated calcium channels, potassium channels, and/or sodium channels.

Certain embodiments of the invention involve modifying a clostridial toxin such that the modified toxin has an altered cell targeting capability for a neuronal or non-neuronal cell of interest. Called re-targeted endopeptidases or Targeted Vesicular Exocytosis Modulator Proteins (TVEMPs), these molecules achieve their exocytosis inhibitory effects by targeting a receptor present on the neuronal or non-neuronal target cell of interest. This re-targeted capability is achieved by replacing the naturally-occurring binding domain of a clostridial toxin with a targeting domain showing a selective binding activity for a non-clostridial toxin receptor present in a cell of interest. Such modifications to the binding domain result in a molecule that is able to selectively bind to a non-clostridial toxin receptor present on the target cell. A re-targeted endopeptidase can bind to a target receptor, translocate into the cytoplasm, and exert its proteolytic effect on the SNARE complex of the neuronal or non-neuronal target cell of interest.

The combination of *botulinum* toxins and endopeptidases allows for dose reduction of active agents (with associated reduction in side effects) as well as possible synergistic effects. Non-paralytic effects, and also possible prophylactic effects especially when used early in the condition can provide further benefits.

An important difference between re-targeted endopeptidases such as TVEMPs and native clostridial toxins is that because the TVEMPs do not target motor neurons, the lethality associated with over-dosing a mammal with a TVEMP is greatly minimized, if not avoided altogether. For example, opioid TVEMPs can be administered at 10,000 times the therapeutically effective dose before evidence of lethality is observed, and this lethality thought to be due to the passive diffusion of the molecule and not via the intoxication process. Thus, for all practical purposes TVEMPs are non-lethal molecules.

Using a combination therapy of *botulinum* toxin with TVEMPs, a lower dose of the toxin can be used to treat the disorder. This will result in a decrease in muscle weakness generated in the compensatory muscles relative to the current treatment paradigm. The assessment for injection would require a careful examination for agonists and compensatory painful muscles.

The molar ratio of *botulinum* toxin to TVEMP in the combination treatment may be a 1:1 ratio; a 1:2 ratio; a 1:5 ratio; a 1:10 ratio; a 1:20 ratio; a 1:50 ratio; a 1:100 ratio; 1:200 ratio; a 1:500 ratio; a 1:1000 ratio; 1:2,000 ratio; a 1:5,000 ratio; or a 1:10,000 ratio.

Certain embodiments of the invention can utilize administration via implant. Implants useful in practicing the methods disclosed herein may be prepared by mixing a desired amount of a stabilized *Botulinum* toxin (such as non-reconstituted BOTOX®) into a solution of a suitable polymer dissolved in methylene chloride. The solution can be prepared at room temperature. The solution can then be transferred to a Petri dish and the methylene chloride evaporated in a vacuum desiccator. Depending upon the implant size desired and hence the amount of incorporated neurotoxin, a suitable amount of the dried neurotoxin-incorporating implant is compressed at about 8000 p.s.i. for 5 seconds or at 3000 p.s.i. for 17 seconds in a mold to form implant discs encapsulating the neurotoxin. See e.g. Fung L. K. et al., Pharmacokinetics of Interstitial Delivery of Carmustine 4-Hydroperoxycyclophosphamide and Paclitaxel From a Biodegradable Polymer Implant in the Monkey Brain, Cancer Research 58;672-684: 1998.

Additionally, in some embodiments, a physician may have to alter dosage in each case in accordance with the assessment of the severity of the condition, as typically done when treating patients with a condition/disorder. Further, in some embodiments, the treatment may have to be repeated at least one additional time, in some cases several times, depending on the severity of the condition and the patient's overall health. If, for example, a patient is not deemed physically suitable for a full administration of *botulinum* toxin, or if a full administration is not desired for any reason, smaller doses on multiple occasions may prove to be efficacious.

Of course, an ordinarily skilled medical provider can determine the appropriate dose and frequency of administration(s) to achieve an optimum clinical result. That is, one of ordinary skill in medicine would be able to administer the appropriate amount of the toxin, for example *Botulinum* toxin type A, at the appropriate time(s) to effectively treat the disorder. The dose of the neurotoxin to be administered depends upon a variety of factors, including the severity of the eye disorder. The dose of the toxins employed in accordance with this invention may be equivalent to the dose of BOTOX® used in accordance with the present invention described herein. In various methods of the present invention, from about 0.01 U/kg (U of *botulinum* toxin per kilogram of patient weight) to about 15 U/kg, of a BOTOX® e.g. *botulinum* toxin type A, can be administered. In some embodiments, about 0.1 U/kg to about 20 U/kg of BOTOX® may be administered. Use of from about 0.1 U/kg to about 30 U/kg of a BOTOX®, is within the scope of a method practiced according to the present disclosed invention. In one embodiment, about 0.1 U/kg to about 150 U/kg *botulinum* toxin, for example type A, may be administered.

Significantly, a method within the scope of the present invention can provide improved patient function.

EXAMPLES

Example 1

A 22 year old woman (occupation executive assistant) reports chest pain, especially upon swallowing. She is diagnosed via a barium swallow as suffering from DES.

Her doctor suggests treatment using localized administration of a *Botulinum* toxin. Endoscopic injections of *Botulinum* type A into the muscle wall are performed as follows:
  30 U at the level of the LES;
  22.5 U 6 cm above the LES;
  17.5 U 12 cm above the LES;
  15 U 18 cm above the LES;
  10 U 24 cm above the LES;
  5 U 30 cm above the LES;
  Total dose 100 U.

Within days, the patient reports a decrease in her symptoms. The patient is evaluated at three months to determine whether another round of injections is necessary.

Example 2

A 48 year old man (occupation construction worker) complains of difficulty in swallowing as well as chest pain. He is diagnosed via intraluminal ultrasound imaging as suffering from nutcracker esophagus.

His doctor suggests treatment using localized administration of a *Botulinum* toxin. Implants comprising the following amounts of *Botulinum* type A are placed into the muscle wall as follows:
  30 U at the level of the LES;
  22.5 U 6 cm above the LES;
  17.5 U 12 cm above the LES;
  15 U 18 cm above the LES;
  10 U 24 cm above the LES;
  5 U 30 cm above the LES;
  Total dose 100 U.

Within days, the patient reports a decrease in his symptoms. The patient is evaluated at three months to determine whether further treatment is necessary.

Example 3

A 18 year old man (occupation construction worker) complains of difficulty in swallowing as well as chest pain. He is diagnosed via intraluminal ultrasound imaging as suffering from nutcracker esophagus.

His doctor suggests treatment using localized administration of a *Botulinum* toxin. Implants comprising the following amounts of *Botulinum* type A are placed into the muscle wall as follows:
- 20 U at the level of the LES;
- 18 U 6 cm above the LES;
- 19 U 12 cm above the LES;
- 12 U 18 cm above the LES;
- 8 U 24 cm above the LES;
- 3 U 30 cm above the LES.

Within days, the patient reports a decrease in his symptoms. The patient is evaluated at three months to determine whether further treatment is necessary.

Example 4

A 22 year old woman (occupation patent lawyer) complains of difficulty in swallowing as well as chest pain. She is diagnosed via intraluminal ultrasound imaging as suffering from DES.

Her doctor suggests treatment using localized administration of a *Botulinum* toxin. Implants comprising the following amounts of *Botulinum* type A are placed into the muscle wall as follows:
- 30 U at the level of the LES;
- 22.5 U 6 cm above the LES;
- 17.5 U 12 cm above the LES;
- 15 U 18 cm above the LES;
- 10 U 24 cm above the LES;
- 5 U 30 cm above the LES.

Within days, the patient reports a decrease in her symptoms. The patient is evaluated at three months to determine whether further treatment is necessary.

Example 5

A 62 year old woman (occupation actress) reports chest pain, especially upon swallowing. She is diagnosed via a barium swallow as suffering from DES.

Her doctor suggests treatment using localized administration of a *Botulinum* toxin. Endoscopic injections of *Botulinum* type A into the muscle wall are performed as follows:
- 30 U at the level of the LES;
- 22.5 U 4 cm above the LES;
- 12.5 U 8 cm above the LES;
- 15 U 12 cm above the LES;
- 7 U 17 cm above the LES;
- 3 U 21 cm above the LES.

Within days, the patient reports a decrease in her symptoms. The patient is evaluated at three months to determine whether another round of injections is necessary.

What is claimed is:

1. A method for treating esophageal spasm, comprising administering a botulinum toxin to the esophagus of a patient suffering therefrom, such administration comprising:
    a) a first administration of between 15 and 25 U at the level of the Lower Esophageal Sphincter (LES);
    b) a second administration of between 10 and 30 U above the site of the first administration; and
    c) a third administration of between 10 and 30 U above the site of the second administration;
    wherein the dose used in the second administration is lower than the dose used in the first administration, and the dose used in the third administration is lower than the dose used in the second administration;
    thereby treating the patient.

2. The method of claim 1, wherein the *botulinum* toxin comprises botulinum toxin type A.

3. The method of claim 2, wherein said first administration comprises administration via injection.

4. The method of claim 3, wherein said first administration comprises administration via intramuscular injection.

5. The method of claim 1, further comprising a fourth administration of between 10 and 30 U above the site of the third administration.

6. A method for treating esophageal spasm, comprising administering a *botulinum* toxin to the esophagus of a patient suffering therefrom, such administration comprising:
    a) a first administration of 30 U of botulinum toxin at the level of the Lower Esophageal Sphincter (LES);
    b) a second administration of 22.5 U of *botulinum* toxin 6 cm above the LES;
    c) a third administration of 17.5 U of *botulinum* toxin 12 cm above the LES;
    d) a fourth administration of 15 U of *botulinum* toxin 18 cm above the LES;
    e) a fifth administration of 10 U of *botulinum* toxin 24 cm above the LES; and
    f) a sixth administration of 5 U of *botulinum* toxin 30 cm above the LES;
    thereby treating the patient.

7. The method of claim 6, wherein the *botulinum* toxin comprises *botulinum* toxin type A.

8. The method of claim 7, wherein said administration comprises administration via injection.

9. The method of claim 6, wherein said administration comprises administration via intramuscular injection.

10. The method of claim 6, wherein said administration comprises administration via implant.

* * * * *